United States Patent [19]

Hatcher

[11] 4,228,309

[45] Oct. 14, 1980

[54] CYCLOHEXANE EXTRACTION TO REMOVE CHLORODIBENZO-P-DIOXINS

[76] Inventor: David B. Hatcher, 8433 Katy Freeway, Houston, Tex. 77024

[21] Appl. No.: 32,100

[22] Filed: Apr. 20, 1979

Related U.S. Application Data

[63] Continuation-in-part of Ser. No. 876,999, Feb. 13, 1978, abandoned.

[51] Int. Cl.$^3$ ............................................... C07C 37/70
[52] U.S. Cl. .................................................... 568/755
[58] Field of Search ........................ 568/755, 776, 774

[56] References Cited

U.S. PATENT DOCUMENTS

| | | | |
|---|---|---|---|
| 2,725,402 | 11/1955 | Britton et al. | 568/755 |
| 3,707,568 | 12/1972 | Michaels et al. | 568/755 |
| 3,839,463 | 10/1974 | Cohn | 568/755 |
| 4,016,047 | 4/1977 | Christena | 568/755 |

Primary Examiner—Warren B. Lone
Attorney, Agent, or Firm—Marshall & Yeasting

[57] ABSTRACT

Chlorodibenzo-p-dioxin impurities are removed from a polychlorophenol that contains at least one chlorodibenzo-p-dioxin as an impurity by preparing an aqueous solution of a water-soluble alkaline salt of the polychlorophenol, mixing the aqueous solution with cyclohexane to extract the dioxins therefrom, decanting the purified aqueous solution from the cyclohexane phase, neutralizing the purified aqueous solution to precipitate the purified polychlorophenol, and separating the precipitate.

7 Claims, No Drawings

CYCLOHEXANE EXTRACTION TO REMOVE CHLORODIBENZO-P-DIOXINS

CROSS REFERENCE TO RELATED APPLICATION

This application is a continuation-in-part of Ser. No. 876,999 filed Feb. 13, 1978 now abandoned.

BACKGROUND OF THE INVENTION

One object of the invention is to obviate the necessity of using expensive vacuum distillation apparatus such as that required by the method disclosed in Christena U.S. Pat. No. 4,016,047.

The methods of purifying trichlorophenol which are described in Michaels U.S. Pat. No. 3,707,568 are not designed to remove chlorodibenzo-p-dioxins. The properties of chlorodibenzo-p-dioxins are so similar to those of polychlorophenols that it is extremely difficult to separate chlorodibenzo-p-dioxin impurities from polychlorophenols by any method of purification heretofore known.

SUMMARY OF THE INVENTION

The present invention is based upon the discovery of a unique relationship between the relative solubilities in water and cyclohexane of an alkaline salt of a polychlorophenol and chlorodibenzo-p-dioxin impurities contained in such salt. This unique relationship makes it possible to use cyclohexane to extract such impurities from an aqueous solution of such a salt.

The ability of cyclohexane to extract a relatively high concentration of chlorodibenzo-p-dioxins from an aqueous solution of an alkaline salt of a polychlorophenol is hard to understand, because the concentration of the cyclohexane solution thus obtained is much higher than the concentration which can be attained by dissolving a chlorodibenzo-p-dioxin directly in cyclohexane.

It has been discovered also that an important improvement in the efficiency of the process is effected by carrying out the additional step of filtering the aqueous solution of the water-soluble alkaline salt before it is extracted with cyclohexane.

DESCRIPTION OF THE PREFERRED EMBODIMENTS

Pentachlorophenol is an example of a polychlorophenol which may be used in the practice of the present invention.

Wood used as a construction material is subject to attack by fungus, termites and various beetles. For that reason, it is necessary to apply a preservative to many wood products, such as lumber, utility poles and railroad ties.

Pentachlorophenol is widely used as a wood preservative, because it gives highly satisfactory results. The amount of solutions of pentachlorophenol used annually in the preservation of wood is measured in hundreds of millions of gallons.

In recent years, concern has arisen concerning the toxic effects of chlorodibenzo-p-dioxins which are contained in commercial pentachlorophenol. These substances are known to cause porphyria and chloracne in industrial workers who are exposed to commercial pentachlorophenol.

The form of pentachlorophenol which is ordinarily used commercially is technical pentachlorophenol, which contains about 10% by weight of a mixture of tetrachlorophenols. Tetrachlorophenols and trichlorophenols may also be purified by the present method.

Technical pentachlorophenol has been found to contain approximately two thousand parts per million of octachlorodibenzo-p-dioxin. Any other chlorodibenzo-p-dioxin in technical pentachlorophenol is usually present in an amount of not more than about 1% of the amount of octachlorodibenzo-p-dioxin. Such other chlorodibenzo-p-dioxins which may be present in technical pentachlorophenol include the hexachloro and the heptachloro derivatives.

In view of these relative amounts of chlorodibenzo-p-dioxins which are present in technical pentachlorophenol, the present method may be considered to be a method of proportionately reducing the content of each chlorodibenzo-p-dioxin in the chlorophenol, to bring the content of each below the desired maximum level. However, the present method also serves to remove other chlorinated impurities which are present in technical pentachlorophenol.

The water-soluble alkaline salts of polychlorophenols which can be used include the magnesium, calcium and ammonium salts, but the alkali metal salts such as the sodium, potassium and lithium salts are more convenient to use because of their higher solubility in water. These salts are prepared in the usual manner by dissolving the polychlorophenol in an aqueous solution of an equivalent amount of a corresponding base such as the hydroxide. An aqueous solution of a carbonate of an alkali metal may also be used. The dissolving may take place at room temperature, but is expedited by heating to an elevated temperature, up to the boiling point of the solution.

For the sake of economy, and to reduce the volume of liquid to be handled, the aqueous solution of the water-soluble alkaline salt of a polychlorophenol preferably is a substantially concentrated solution. In the case of an aqueous solution of sodium or potassium pentachlorophenate, the polychlorophenol content of the solution may be as high as about 30%. However, it is possible to employ an aqueous sodium or potassium polychlorophenate solution having a polychlorophenol content as low as about 0.5%. Other alkaline salts of polychlorophenols would be employed in concentrations at the lower end of this range, because of their lower solubility.

The extraction with cyclohexane, if carried out as a batch process, preferably is carried out by extracting the aqueous solution with successive batches of a volume of cyclohexane approximately equal to the volume of the aqueous solution, until the content of octachlorodibenzo-p-dioxin in the cyclohexane extract is suitably small, indicating that the last extraction with cyclohexane has removed substantially all of the chlorodibenzo-p-dioxins from the aqueous solution. Although the volume ratio of cyclohexane to aqueous solution in such a batch extraction preferably is about 1:1, it may vary from 1:10 to 10:1.

The extraction step also may be carried out as a continuous liquid-liquid extraction, in which a stream of the aqueous solution is mixed with an approximately equal stream of cyclohexane and pumped to a relatively quiet zone in a vessel where the aqueous solution and the cyclohexane may be separately removed through two outlets located at different levels in the vessel. In such a continuous method, a substantial proportion of the aqueous solution flowing from the quiet zone may be recycled, while the cyclohexane removed from the quiet zone may be purified by distillation in order to provide a fresh supply of cyclohexane for reuse in the process.

In one version of such a continuous method, the aqueous solution is introduced into a packed column a short distance below the top of the column, while the cyclohexane is introduced a short distance above the bottom of the column. The purified aqueous solution is tapped off at the bottom of the column, and the used cyclohexane overflows at the top.

The ratio between the volume of cyclohexane and the volume of aqueous solution used in continuous extraction preferably is about 1:1, but may range from 1:10 to 10:1.

In order to precipitate the purified polychlorophenol from the final aqueous solution, it is most convenient to add a strong mineral acid such as hydrochloric or sulfuric acid. The precipitated polychlorophenol may then be separated by filtration, and may be washed with water. The dried product may then be pelleted in any desired manner, to produce dust-free pellets which are the most desirable form of such a product.

In the step of adding an acid to the purified aqueous solution in order to precipitate the polychlorophenol, an amount of acid sufficient to precipitate polychlorophenols is added. Thus the amount of acid added may be an amount sufficient to neutralize the base used in preparing the salts of polychlorophenols. For example, if the alkaline salt in the purified aqueous solution is sodium pentachlorophenate, an amount of hydrochloric acid may be added sufficient to convert all of the sodium pentachlorophenate to sodium chloride and pentachlorophenol.

EXAMPLE 1

Technical pentachlorophenol (15 parts by weight) was added to 85 parts by weight of an aqueous solution at 60° C., containing an amount of sodium hydroxide equivalent to the amount of pentachlorophenol. The solution was then stirred until the pentachlorophenol has dissolved.

After cooling, 25 ml of the aqueous solution was added to a 125 ml separatory funnel together with 25 ml of cyclohexane. The separatory funnel was shaken for two minutes, and the cyclohexane layer and the aqueous layer then were allowed to separate. The cyclohexane layer was removed and filtered through anhydrous sodium sulfate, and was then analyzed to determine its content of octachlorodibenzo-p-dioxin. The aqueous layer was returned to the separatory funnel, together with an equal volume of fresh cyclohexane. The extraction procedure was repeated three times, for a total of four extractions.

Since the pentachlorophenol content in the aqueous solution was 15% by weight, the 25 ml of solution used in this example contained about 3.75 grams of pentachlorophenol.

Table 1 below shows the octachlorodibenzo-p-dioxin content in milligrams contained in the 25 ml of cyclohexane from each of the four extractions, after separation from the aqueous phase. In addition to showing the amount of the dioxin in milligrams contained in the cyclohexane layer from each extraction, table 1 also expresses the same quantity of dioxin as parts per million of the pentachlorophenol contained in the 25 ml of aqueous solution.

TABLE I

| Extraction Number | OCDD Removal Weight mg | OCDD in PCP mg OCDD/kg PCP |
|---|---|---|
| 1 | 7.00 | 1870 |
| 2 | 0.975 | 260 |
| 3 | 0.550 | 146 |
| 4 | 0.200 | 53 |
| Total | 8.725 | 2329 |

Table 1 shows that in this example, 2329 parts per million of the dioxin were removed from the pentachlorophenol. This amount of the dioxin is close to the total dioxin content of the pentachlorophenol, indicating that the removal of octachlorodibenzo-p-dioxin from pentachlorophenol by this method was highly efficient.

EXAMPLE 2

A procedure was carried out as described in Example 1, except that the procedure was continued for a total of eight extractions. As a further check, the same procedure was carried out again for a total of six extractions. In this case, however, the dioxin content of the cyclohexane layer from the first and third extractions was not determined.

The results obtained are shown in Table 2 below.

TABLE 2

| Extraction Numbers | Weight OCDD Removed mg | OCDD in PCP mg/kg | Average Removed mg/kg |
|---|---|---|---|
| 1 | 6.45 | 1720 | 1720 |
| 2 | 1.55 | 412 | 397 |
| 2 | 1.43 | 382 | |
| 3 | 0.17 | 45 | 45 |
| 4 | 0.10 | 27 | 40 |
| 4 | 0.20 | 54 | |
| 5 | 0.07 | 19 | 17 |
| 5 | 0.06 | 15 | |
| 6 | 0.06 | 15 | 13 |
| 6 | 0.04 | 11 | |
| 7 | 0.04 | 11 | 11 |
| 8 | 0.08 | 20 | 20 |
| | | Total | 2263 |

EXAMPLE 3

This example demonstrates the improved results which are obtained when solid impurities are filtered from the aqueous solution before it is extracted with cyclohexane.

Two procedures were carried out, each of which was the same as that described in Example 1, except that in each case, the original preparation of the sodium pentachlorophenate solution was followed by filtration of the aqueous solution through Whatman 541 filter paper, and then extraction was carried out on the filtered aqueous solution with six successive 25 ml portions of cyclohexane.

Table 3 below shows that the filtration of the aqueous solution of sodium pentachlorophenate removed a substantial proportion of the octachlorodibenzo-p-dioxin which had been originally present in the pentachlorophenol. As a result, the removal of the dioxin in the six extractions carried out by this procedure was more complete than the removal which was obtained in Examples 1 and 2.

TABLE 3

| Extraction Numbers | Weight OCDD Removed mg | OCDD in PCP mg/kg | Average Removed mg/kg |
|---|---|---|---|
| 1 | 1.87 | 499 | 544 |
| 1 | 2.21 | 589 | |
| 2 | 0.175 | 46.7 | 77.4 |
| 2 | 0.405 | 108 | |
| 3 | 0.065 | 17.3 | 17.6 |
| 3 | 0.068 | 18.0 | |
| 4 | 0.018 | 4.7 | 6.0 |
| 4 | 0.028 | 7.3 | |
| 5 | 0.002 | 2.0 | 2.4 |
| 5 | 0.003 | 2.7 | |
| 6 | 0.001 | 0.3 | 0.4 |
| 6 | 0.002 | 0.5 | |
| | | Total | 648 |

A sample consisting of 25 ml of the purified solution of sodium pentachlorophenate prepared as described above was mixed with 10 ml of concentrated hydrochloric acid, causing precipitation of pentachlorophenol. The purified pentachlorophenol precipitate was recovered by filtering through Whatman 541 filter paper, washing with water and drying.

I claim:

1. A method of removing chlorodibenzo-p-dioxin impurities from a water-soluble alkaline salt of a polychlorophenol that contains up to about two parts of at least one chlorodibenzo-p-dioxin per thousand parts of polychlorophenol, as an impurity, comprising the steps of preparing an aqueous solution of such a salt having a polychlorophenol content from about 0.5% to about 30%, at a temperature from room temperature to the boiling point of the solution, mixing the aqueous solution with one-tenth to ten times its volume of cyclohexane to extract the dioxins therefrom, and decanting the purified aqueous solution from the cyclohexane phase.

2. A method according to claim 1 comprising the step of filtering solid impurities from the aqueous solution before it is mixed with cyclohexane.

3. A method of removing chlorodibenzo-p-dioxin impurities from a polychlorophenol that contains at least one chlorodibenzo-p-dioxin as an impurity, comprising the steps of preparing a water-soluble alkaline salt of the polychlorophenol, removing said impurities from said salt by the method of claim 1, neutralizing the purified aqueous solution to precipitate the purified polychlorophenol, and separating the precipitate.

4. A method according to claim 3 wherein the polychlorophenol is pentachlorophenol.

5. A method according to claim 3 comprising the step of filtering solid impurities from the aqueous solution before it is mixed with cyclohexane.

6. A method according to claim 1 wherein the salt is an alkaline salt of the class consisting of sodium, lithium, potassium, calcium, magnesium and ammonium salts.

7. A method according to claim 1 wherein a stream of the aqueous solution is continuously mixed with a stream of cyclohexane, and the mixture is allowed to separate by gravity.

* * * * *